(12) United States Patent
Goergen et al.

(10) Patent No.: US 11,559,214 B2
(45) Date of Patent: Jan. 24, 2023

(54) DIAGNOSTIC AND THERAPEUTIC DEVICE FOR COMPROMISED VASCULAR HEMODYNAMICS ANALYSIS

(71) Applicant: Purdue Research Foundation, West Lafayette, IN (US)

(72) Inventors: Craig J. Goergen, West Lafayette, IN (US); Kirk Solon Foster, West Lafayette, IN (US); David Reuter, West Lafayette, IN (US); George R. Wodicka, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 417 days.

(21) Appl. No.: 16/638,812

(22) PCT Filed: Aug. 29, 2018

(86) PCT No.: PCT/US2018/048549
§ 371 (c)(1),
(2) Date: Feb. 13, 2020

(87) PCT Pub. No.: WO2019/050738
PCT Pub. Date: Mar. 14, 2019

(65) Prior Publication Data
US 2021/0127982 A1  May 6, 2021

Related U.S. Application Data

(60) Provisional application No. 62/554,527, filed on Sep. 5, 2017.

(51) Int. Cl.
*A61B 5/02*   (2006.01)
*A61B 5/022*  (2006.01)
*A61B 5/00*   (2006.01)

(52) U.S. Cl.
CPC ............ *A61B 5/022* (2013.01); *A61B 5/0004* (2013.01); *A61B 5/0022* (2013.01);
(Continued)

(58) Field of Classification Search
CPC ..... A61B 5/022; A61B 5/0004; A61B 5/0022; A61B 5/7275; A61B 5/7405; A61B 5/742;
(Continued)

(56) References Cited

U.S. PATENT DOCUMENTS

2008/0082001 A1  4/2008  Hatlestad
2011/0009718 A1  1/2011  Gavish
(Continued)

FOREIGN PATENT DOCUMENTS

JP    2004195070 A    7/2004

OTHER PUBLICATIONS

European Patent Office Search Report, dated Apr. 12, 2021.

*Primary Examiner* — Tanmay K Shah
(74) *Attorney, Agent, or Firm* — Purdue Research Foundation

(57) ABSTRACT

An integrated triad system to measure a patient's blood pressure at different body positions, to instruct the patient when to move from one position to the next to alleviate vascular hypertension based on an algorithm stored in the system calculating blood pressure changes and predictive risk, and to transmit the result to a remote medical location. Using the integrated triad system to perform the test over a period can increase test sensitivity by accommodating the variable onset of the disease.

14 Claims, 2 Drawing Sheets

(52) U.S. Cl.
CPC ............ *A61B 5/7275* (2013.01); *A61B 5/742* (2013.01); *A61B 5/7405* (2013.01); *A61B 2562/0219* (2013.01)

(58) Field of Classification Search
CPC .......... A61B 2562/0219; A61B 5/7455; A61B 5/746; A61B 5/1116; A61B 5/4343; A61B 5/6823; A61B 5/6831
USPC ......................................................... 600/490
See application file for complete search history.

(56) References Cited

U.S. PATENT DOCUMENTS

| | | | |
|---|---|---|---|
| 2015/0164404 A1* | 6/2015 | Euliano | G16H 40/63 600/301 |
| 2015/0305668 A1 | 10/2015 | Dugan | |
| 2016/0029904 A1* | 2/2016 | Quinn | A61B 5/11 600/499 |
| 2016/0157735 A1* | 6/2016 | Zhang | A61B 5/1118 600/595 |
| 2016/0302677 A1* | 10/2016 | He | A61B 5/1102 |
| 2016/0374608 A1* | 12/2016 | Dugan | A61B 5/746 600/301 |
| 2017/0245769 A1* | 8/2017 | Niehaus | A61B 5/117 |
| 2018/0234496 A1* | 8/2018 | Ratias | A63F 13/60 |

\* cited by examiner

DIAGNOSTIC AND THERAPEUTIC DEVICE FOR COMPROMISED VASCULAR HEMODYNAMICS ANALYSIS

CROSS-REFERENCE TO RELATED APPLICATION

The present U.S. patent application is a national stage entry under 35 U.S.C. § 371(b) of International Application No. PCT/US18/48549, filed on Aug. 29, 2018, which relates to and claims the priority benefit of U.S. Provisional Application No. 62/554,527, filed Sep. 5, 2017, the contents of which are hereby incorporated by reference in their entireties.

FIELD OF INVENTION

This disclosure relates to a diagnostic and therapeutic tool for the global care of patients with compromised venous hemodynamics in general. Specifically, the disclosure integrates a device to measure patient blood pressure, a sensor to assess the patient body position, and a processing unit that analyzes the change in blood pressure in the context of patient position. The device then communicates guidance to better manage relevant clinical conditions.

BACKGROUND

In the cardiology and nephrology communities, it is known that increased intrarenal pressure causes hypertension, a condition also known as Page kidney. Page kidney is not only caused by external compression or intra-renal pathology, venous outflow obstruction also causes Page kidney physiology, which is not realized by medical community. The hypertension is renin-mediated acutely, but ischemia-mediated chronically. In the setting of pregnancy, the left renal vein is vulnerable to be compressed between the gravid uterus and the anterior wall of the aorta starting after 20 weeks of gestation. This subset of women with inadequate ipsilateral collateral venous circulation is most vulnerable to venous outflow obstruction. Maternal recumbent position directly affects renal hemodynamics, with the supine position making the kidneys most vulnerable to Page kidney physiology.

Previously published work has demonstrated that when a shift from the left lateral recumbent to the supine position is associated with an elevation of diastolic BP of 20 mmHg or more, the Positive Predictive Value (PPV) of developing preeclampsia is as high as 93%. This test is referred to as the supine pressor test (SPT). Furthermore, previous work has demonstrated that when women are identified as being at risk via the SPT, simply resting in the lateral recumbent position for an additional 4-6 hours per day is sufficient to prevent preeclampsia in the majority of cases. The impact of maternal recumbent position on renal hemodynamics is the presumed mechanism of the diagnostic and therapeutic observations. The SPT, which historically was performed between the 28-32 weeks gestation, initially fell out of favor, not because it lacked specificity, but because it demonstrated inadequate sensitivity and because heterogeneous methodology diminished the PPV.

Venous hemodynamics can be affected in patients with many conditions including those who are either pregnant and/or who demonstrate central obesity (i.e., abdominal mass effect associated with clinical condition). The effect on venous hemodynamics can cause both an increase and/or a decrease in blood pressure. A change in recumbent position is a common trigger to cause a change in blood pressure (e.g., lateral recumbent to supine). The change in blood pressure usually takes a variable amount of time to manifest itself; thus, a device that simultaneously monitors the triad of blood pressure (systolic/diastolic), body position, and time and communicates pertinent information to the healthcare provider and patient would help diagnose, treat, and/or manage a variety of clinical conditions

SUMMARY OF THE INVENTION

This disclosure provides device and method of using combinations of an automatic noninvasive blood pressure measurement (NIBP) and algorithms to compare blood pressure in various patient body positions. The device and method can be used to predict high blood pressure risk patient, provide necessary surveillance and therapeutic recommendations to the patient population in a cost effective, low-stress environment.

Briefly, the disclosure provides an integrated triad comprising of a blood pressure (BP) measurement device, a body position sensor and a data processor unit, wherein the data processor unit performs analysis/communication tasks based on the blood pressure measurement changes on different body posture positions in relation to available medical knowledge of pathological conditions.

In some embodiment, the aforementioned blood pressure measurement unit is a sphygmomanometer, the body postural measurement unit is an accelerometer, and the data processor unit comprising algorithms interpreting blood pressure measurement changes and correlating the changes in different postural positions to available medicinal knowledge of pathological conditions.

One aspect of the disclosure provides an automated system to improve the accuracy of diagnosis, monitoring and therapy to a patient with compromised vascular hemodynamics. The system comprising:

a. an automatic non-invasive blood pressure measurement unit;

b. an body position sensor system to precisely detect the patient's position;

c. an algorithm to compare blood pressure in different positions of the patient;

d. a voice and/or image commands unit that communicates with the patient to adjust position in a timely manner to obtain additional blood pressure readings to be incorporated into the algorithm for determination of the stable patient blood pressure; and e. a telemetry unit to transmit the diagnosis data to a remote clinic care.

In some preferred embodiment, the aforementioned patient is a pregnant women and the diagnosis is for pregnancy associated hypertension and/or preeclampsia.

In some preferred embodiment, the aforementioned patient has central obesity and hypertension.

In some preferred embodiment, the aforementioned algorithm provides a clinically meaningful positive predictive value.

In some preferred embodiment, the body position sensor is an accelerometer.

In some preferred embodiment, the aforementioned algorithm recognizes a significant elevation of diastolic blood pressure (e.g., greater than 20 mmHg) associated with a change from lateral recumbent to supine position.

In some preferred embodiment, the aforementioned algorithm is stored in a smartphone.

In some preferred embodiment, the aforementioned voice and/or image commands unit is a smartphone.

In some preferred embodiment, the aforementioned voice and/or image command unit has an auditory or a vibratory component to wake up the patient in an non-acceptable body position for a prolonged time.

One aspect of the disclosure provides a method to accurately predict pregnancy associated hypertension in a pregnant woman. The method comprises:

a. measuring the blood pressure of the woman in her lateral decubitous position at periodic intervals to obtain a stable blood pressure reading;

b. measuring the blood pressure of the woman in her supine position as in step a, wherein the position in decubitous state and supine state is determined by a body position sensor and communicated to the woman by a voice/image unit;

c. using an algorithm to compare the readings in step a and step b to determine if the woman has reached the threshold of pregnancy associated hypertension; and d. optionally connecting the algorithm determined outcome to a voice/image unit to convey the message to the woman or transmit the outcome to a remote clinic care unit.

In some preferred embodiment the aforementioned threshold of pregnancy related hypertension is about 5-10 mmHg, about 20 mmHg, or exceeding about 20 mmHg diastolic blood pressure reading difference between the stable lateral decubitous positon and stable supine position.

Another aspect of the disclosure provides a method of monitoring a patient's blood pressure away from a clinical setting. The method comprises:

a. measuring the blood pressure of the patient from the left or right lateral decubitous position for periodic intervals, e.g. at least approximately 15 minutes with every 5 minutes interval to obtain a stable blood pressure reading;

b. measuring the blood pressure of the patient from the supine position as in step a, wherein the position in decubitous state and supine state is determined by a body position sensor and communicated to the woman by a voice/image unit;

c. using an algorithm to compare the readings in step a and step b to determine if the patient has any risk of hypertension; and d. conveying the outcome in step c to the patient via a voice/image unit and to the clinical setting.

Yet another aspect of the disclosure provides a method of providing therapeutic recommendations away from a clinical setting to a patient with high blood pressure risk. The method comprises:

a. measuring the blood pressure of the patient from the lateral decubitous position for periodic intervals, e.g. at least approximately 15 minutes with every 5 minutes interval to obtain a stable blood pressure reading;

b. measuring the blood pressure of the patient from the supine position as in step a, wherein the position in decubitous state and supine state is determined by a body position sensor and communicated to the woman by a voice/image unit;

c. using an algorithm to compare the readings in step a and step b to determine if the patient has any risk of hypertension;

d. optionally reporting the outcome of step c to the clinical setting for further analysis; and e. using the voice/image unit to command the patient to stay in a position for a prolonged time period to reduces the high blood pressure.

In some preferred embodiment the aforementioned method uses the voice/image units that has additional vibratory component to wake up the patient in a non-acceptable body position for too long.

These and other features, aspects and advantages of the present invention will become better understood with reference to the following figures, associated descriptions and claims.

DETAILED DESCRIPTION

Figure 1:
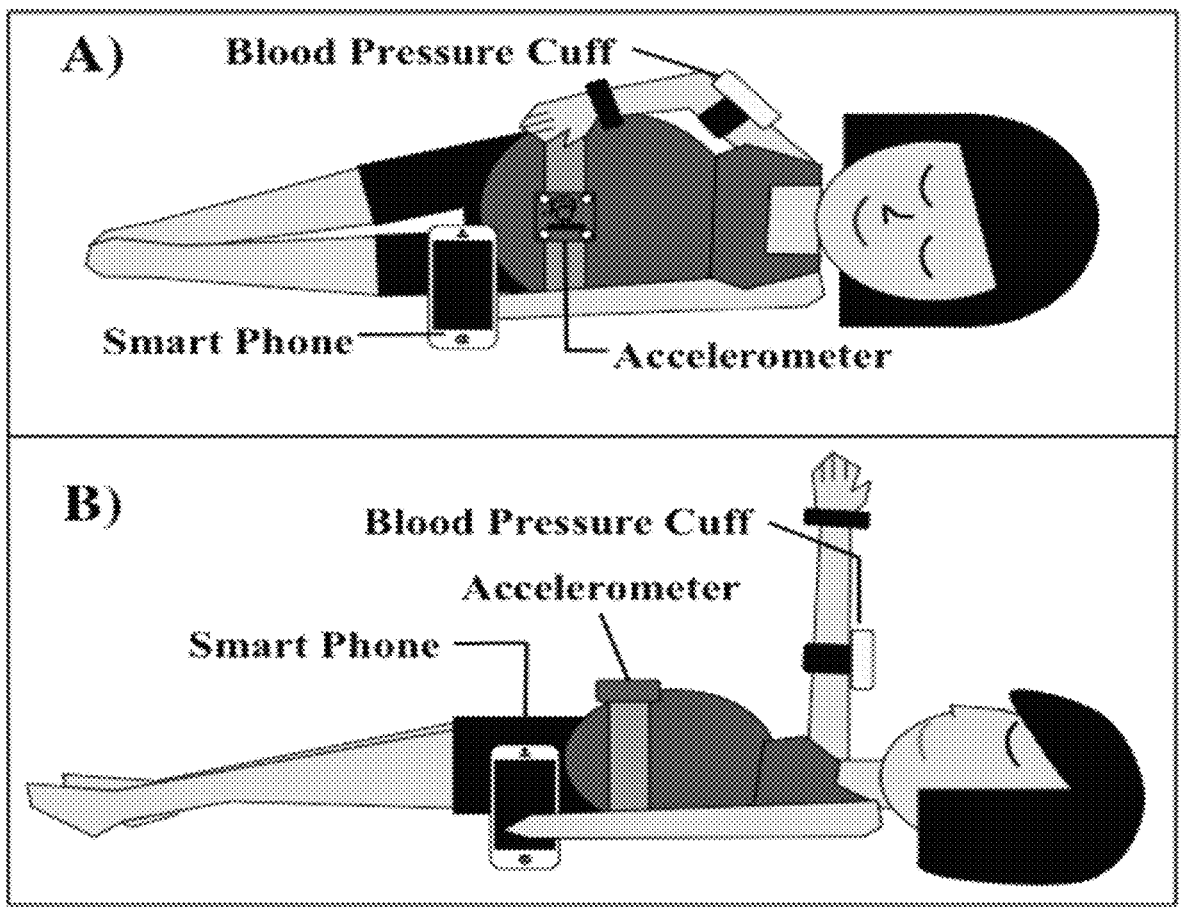
FIG. 1. Schematic of wearable system with patient in both (A) lateral recumbent and (B) supine positions.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

As used herein, "supine" refers to more than just 'flat' on one's back. It is understood as pregnancy develops, laying fully supine could occlude vena cava flow and cause decreased blood pressure. Therefore, supine can include a mild/modest degree of left lateral tilt, which is physiologically wise.

As used herein, "voice/image unit to command" may include a system that communicates with an individual who has been in a non-acceptable body position for too long. The communication with these people can be using auditory or vibratory means to wake them up, and tell them how to optimize position by voice or image.

The morbidity and mortality associated with preeclampsia is staggering. The physiology of the Page kidney, a condition in which increased intrarenal pressure causes hypertension, appears to provide a unifying framework to explain the complex pathophysiology. Page kidney hypertension is renin-mediated acutely and ischemia-mediated chronically. Renal venous outflow obstruction also causes a Page kidney phenomenon, providing an explanation for the increased vulnerability of a subset of women who have what we are describing as a "renal compartment syndrome" due to inadequate ipsilateral collateral renal venous circulation consistent with well-known variation in normal venous anatomy.

Mechanical compression of the left renal vein by the gravid uterus involving a kidney made vulnerable by inadequate ipsilateral collateral venous circulation causes renal venous outflow obstruction, increased intrarenal pressure, and hypertension. Persistent obstruction causes renal compartment syndrome leading to preeclampsia. There is a need to provide stress free devices and methods to accurately predict preeclampsia in pregnant population In this disclosure, a system to measure blood pressure and body position is conceptualized. The proposed system will instruct a patient when to move from one position to the next, then transmits the calculations of blood pressure changes and predictive risk using a smartphone or other algorithm bearing device to a remote medical location or directly to the subject patient. Performing the test sequentially over a matter of months is likely to increase test sensitivity by accommodating the variable onset of the disease.

For example, there are other relevant clinical conditions that are similar to preeclampsia for which an automated blood pressure-body position (Auto-BPBP) device may have important clinical applicability: such as Varicose Veins, Pelvic Congestion Syndrome, Supine Hypotensive syndrome and Renal Insufficiency. While obstruction to renal venous flow causes hypertension due to the renal neurohormonal system that is affected, obstruction to vena cava flow can cause hypotension (due to decreased preload), and the venous congestion that results contributes to the development of conditions like varicose veins and pelvic congestion syndrome.

In addition, complications resulted from obesity include hypertension, hypotension, renal insufficiency and lower extremity edema. All these pathophysiology symptoms involved some common mechanisms. For example, in the case of hypertension, the chain of events can be described as following: Compression of the renal vein by a mass effect (gravid uterus and/or central obesity)→renal venous outflow obstruction→Increased intra-renal pressure→Decreased renal arterial flow→Activation of the Renin-Angiotensin-Aldosterone system (RAAS) as well as activation of the sympathetic nervous system (SNS (Due to stretch of renal capsule and reduced flow thru renal artery))→RAAS/SNS mediated hypertension. Note the left renal vein is most vulnerable to compression as it crosses the midline to the right sided inferior vena cava (IVC); furthermore, the left renal vein is less vulnerable when a patient rests in the lateral recumbent position, or when they rest prone (with abdomen suspended as in a pregnancy massage table), and the left renal vein is most vulnerable when a patient lies primarily supine). With chronic outflow obstruction, the etiology of hypertension evolves from RAAS mediated to ischemia mediated. Specifically, chronic increased intra-renal pressure→renal cell injury/ischemia→release of endothelin (potent vasoconstrictor)→hypertension. For obesity related hypertension, the shift from RAAS mediated to Ischemia mediated hypertension may underlie the evolution from dipper hypertension (blood pressure lower at night) to non-dipper hypertension (blood pressure elevated whether sleeping or not). Furthermore, this underlying physiology may explain why renal artery denervation is sometimes efficacious (RAAS/SNS mediated hypertension) but not universally efficacious (doesn't factor in the ischemia etiology of hypertension). A device that is able to differentiate RAAS/SNS hypertension from Ischemia mediated hypertension also has clinical value. Lastly, since a patient's blood pressure can be normal in the lateral recumbent position, but acutely elevated when the patient shifts from their side to their back, a device that correlates body position, blood pressure, and temporal changes of blood pressure has significant diagnostic and therapeutic clinical utility. Note too that the elevation in blood pressure is sometimes noted more in the diastolic pressure than the systolic pressure. An independent analysis of both pressures provides the greatest clinical utility.

In the event of hypotension, systemic hypotension is most frequently caused by the mass effect (gravid uterus or central obesity) occluding vena cava flow when the patient is essentially supine. This partial reduction in vena cava flow decreases venous return to the heart (preload is decreased) resulting in systemic hypotension. In addition to causing hypotension, compromised vena cava flow can result in a variety of clinical sequelae including but not limited to varicose veins, pelvic congestion syndrome, lower extremity edema, risk for deep venous thrombosis. Thus, in theory, when the compromised venous flow results in tissue hypoperfusion and relative ischemia, the ischemia contributes to insulin resistance and is thus involved in the pathophysiology of both Type II diabetes and Gestational diabetes.

Therefore, a device that detects compromised venous flow as diagnosed by hypotension (or hypotension associated with increased heart rate) may help to reduce or alleviate medical conditions associated with venous stasis. The goal is to develop a device that will help to predict when renal venous flow obstruction contributes to elevated blood pressure.

In this disclosure, we propose an integrated triad of blood pressure device, a body position sensor, and data processor to facilitate collection, interpretation and communication of a patient's blood pressure, body position, and temporal changes in blood pressure and/or body position that may warrant clinical intervention. The data collected (at any location) with any postural measurement device and interpreted in this triad system may be used for any diagnosis, monitoring, and therapy purposes (again at any body location) and an analytical/communication device of any kind, with the sphygmomanometer plus accelerometer plus smartphone as an exemplar.

The design of the disclosed device is intended to improve the technique of the Roll Over test using an engineered algorithm. The voice or visual command can instruct the patient/person relevant to performing the Roll Over Test (Supine Pressor Test). The blood pressure cuff, also known as sphygmomanometer, is used to physically measure blood pressure. The body position sensor, for example, an accelerometer ensures patient is in the proper position (for example, left lateral, supine, prone, supine with modest degree of left lateral tilt to ensure adequate venous flow. A signal/analyzer is used to compare blood pressure data to ensure adequate performance of Roll Over Test and to determine whether test result is positive or negative. The communication means, if needed, can program data to be transmitted to doctors or nurse practitioners in a clinic setting.

As described above, the core components of the proposed system include a blood pressure measurement device, an accelerometer body position sensor and a data processor. Each of their core functionalities are listed below for an example hypertension application.

A sphygmomanometer is used to ensure accurate blood pressure acquisition and the level of cuff relative to the heart does not confound the data with alteration of body position.

An accelerometer is used to determine precise position of the patient. For the classic supine pressor test, confirm that the patient rests in the lateral recumbent position until the patient's blood pressure is stable (e.g., assessed by serial BP measures taken approximately every 5 minutes until final 2 measures show sufficient reproducibility), then confirm that the patient shifts into the supine position.

For pregnant women for whom the mass effect of the gravid uterus is going to increase further from 20-40 weeks gestation, consider modifying the supine position to include a modest (e.g. 10-20) degrees of left lateral tilt so as to maximize effect of pressure on the left renal venous flow transiently, but not compromise IVC flow.

A data Processor is used to compare serial blood pressure measurements (including systolic and diastolic analyses separately), and calculate whether or not there are 'clinically significant changes.' For the pregnancy related supine pressor test, the first serial blood pressure measures acquired approximately every 5 minutes are repeated until a stable 'resting' blood pressure is acquired. Subsequently, that 'final, stable' blood pressure is compared to the blood pressure obtained ~5 minutes after shifting from lateral recumbant to supine position.

Figure 2:
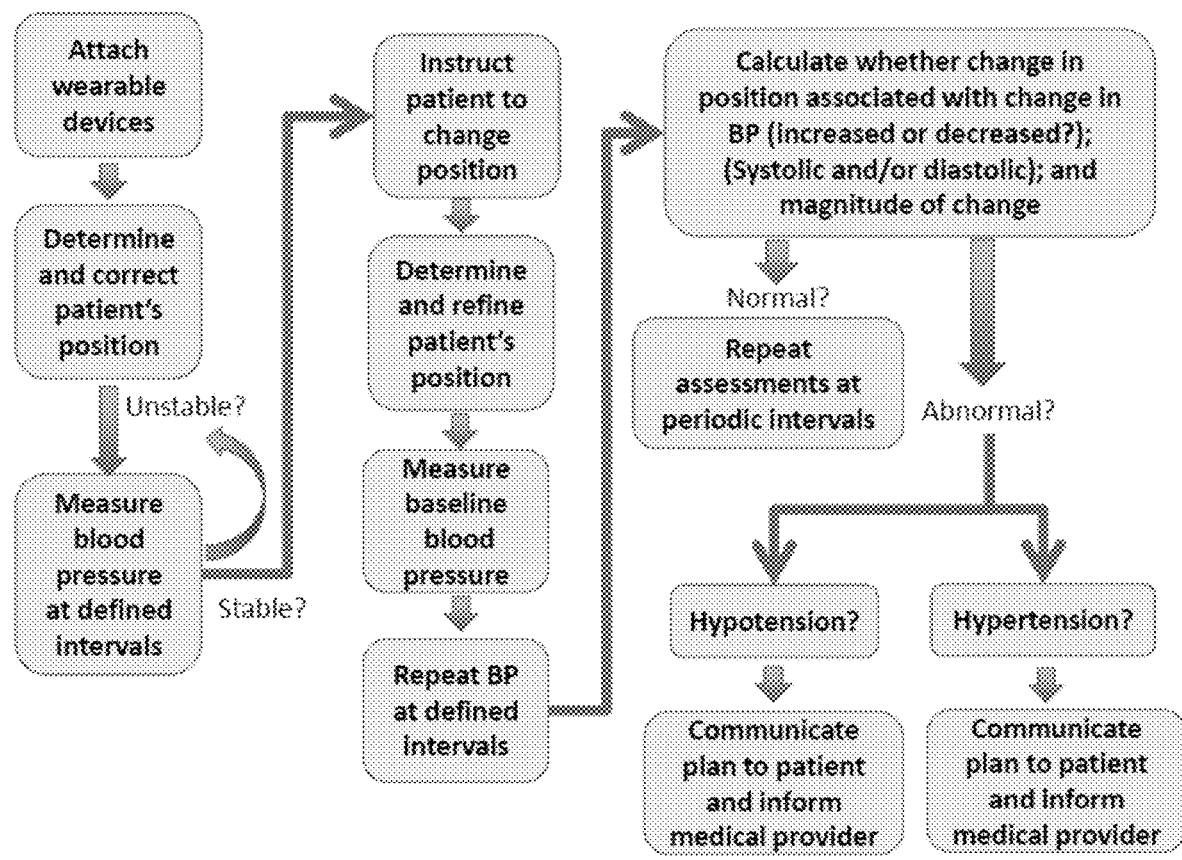
FIG. 2. A flow chart of an exemplary algorithm to predict when venous obstruction contributed to elevated blood pressure.

It is contemplated an algorithm is used to compare different blood pressure measures relative to both the position that they were acquired in, and the time that they were acquired. An exemplary algorithm is illustrated in FIG. 2.

It is also contemplated to have a communication feature that is able to communicate both blood pressure measurement readings and the differences at different positions to the patient, as well as to a remote medical home. The communication to the patient can be through text, auditory, or graphic images. The communication to a remote medical home can be through telemetry. Additionally, we envision a system that a person who has previously been diagnosed as 'vulnerable' can wear while sleeping to ensure that they remain in a 'therapeutic position.' (e.g., to ensure the individual does not inadvertently roll from their side to their back for an extended period of time while they are sleeping). The device should be able to communicate with the individual using a range of body senses (Auditory (voice, chimes, music, etc) Vibratory (rhythmic or non-rhythmic, varying degree of intensity), temperature (unlikely modality, but theoretical possibility).

If the diagnostic detection analysis suggests a clinical issue (e.g., diastolic blood pressure elevated 20 mmHg 5 minutes after shifting from the lateral recumbent to the supine position), then the communication feature is able to instruct the patient to rest in a 'therapeutic position' for a predefined duration and frequency. An example of a predefined therapeutic position/duration would be 4 hours in the lateral recumbent position. The accelerometer would interface with the data processor to ensure adherence to the therapeutic position. Functionally it should be included to accommodate when a patient is sleeping and can't monitor their position easily. The system may have a 'vibratory' component that is able to wake the patient sufficiently from sleep to ensure that they reposition to their side 'cheating toward their tummy' (rather than cheating toward their back) in order to ensure therapeutic compliance.

If the diagnostic detection analysis suggests there is a 'trend toward' a clinically significant elevation in blood pressure (e.g., diastolic blood pressure increases by 15 mmHg rather than 20), then the system may instruct the patient to increase the frequency of diagnostic surveillance (e.g., monitor blood pressure weekly rather than monthly (during second trimester), or daily rather than weekly (in third trimester).

If the diagnostic detection algorithm notes that there is a progressive elevation of systemic pressure (obtained while patient is resting on their side) despite resting for an amount of time in the lateral recumbent position, then the device may communicate to the patient (in combination and coordination with the remote medical home) to either increase the duration in the lateral recumbant position (e.g., from 4 to 8 hours/day), or to rest for a certain duration and frequency in the prone position (e.g., 2 hours TID) using custom cushions that allow for the abdomen to "fall away from" the left renal vein, thus decreasing the renal venous obstruction.

In the example of patients with central obesity, the system could be used to compare rest in the supine vs lateral recumbent vs prone position for variable amounts of time to determine if there is a change in blood pressure associated with the different positions. The information may be used to select the subset of patients who could benefit from a renal vein stent to treat their obesity-related hypertension (e.g., those whose hypertension appears to be RAAS/SNS mediated, note ischemia mediated.

The interface between the three major components of the system can confirm that the traditional supine pressor test is performed with the meticulous attention to detail required to ensure optimal positive predictive value (e.g., relationship of blood pressure cuff to heart is controlled; stable blood pressure is achieved prior to a change in position, accurate calculation of BP differential is tabulated).

The fidelity of the accelerometer is able to detect precise position (body angle) and coach a pregnant woman to rest on her side angled toward her front (to optimize renal hemodynamics) rather than angled toward her back (progressive risk of compromising venous flow.)

The triad system may avoid clinical setting inconvenience and inaccuracies related to blood pressure symptoms and provides flexibility to the patients and clinics on accurate diagnosis, surveillance and therapeutic options.

The invention claimed is:

1. An integrated triad comprising
    a sphygmomanometer;
    an accelerometer to determine and ensure the patient's precise body positions, wherein body positions are left lateral, right lateral, supine, and prone;
    a data processor unit comprising algorithms to analyze blood pressure measurement changes and correlate the blood pressure changes in different postural positions in relation to available medicinal knowledge of pathological conditions comprising compromised vascular hemodynamics; and
    a voice and/or image command unit to communicate pertinent information to the patient or clinic care.

2. The integrated triad according to claim 1, wherein the pathological condition is pregnancy or obesity-related hypertension.

3. An automated test system to improve the accuracy of diagnosis of blood pressure abnormality in a patient, comprising:
    a. an automatic non-invasive blood pressure measurement unit;
    b. an accelerometer to precisely detect the patient's lateral recumbent, supine or prone position;
    c. an algorithm to perform analysis of blood pressure measurement changes by comparing the blood pressure measurements in different positions of the patient;
    d. a voice and/or image command unit, which communicates with the patient to adjust position in a timely manner to obtain additional blood pressure readings to be incorporated into the algorithm for a determination of a stable patient blood pressure measurement and which has a vibratory component to wake up the patient in a non-acceptable body position for a prolonged time; and
    e. a telemetry unit to transmit the diagnosis data to remote clinic care.

4. The automated test system according to claim 3, wherein the patient is a pregnant women and the diagnosis is for pregnancy associated hypertension and/or preeclampsia.

5. The automated test system according to claim 3, wherein the patient has central obesity and hypertension.

6. The automated test system according to claim 3, wherein the algorithm provides a positive predictive value.

7. The automated test system according to claim 3, wherein the algorithm recognizes clinically significant elevation of diastolic blood pressure in at least two stable positions.

8. The automated test system according to claim 3, wherein the algorithm is stored in a smartphone.

9. The automated test system according to claim 3, wherein the voice and/or image command units is a smartphone.

10. A method to accurately predict pregnancy associated hypertension in a pregnant woman, comprising:
   a. measuring the blood pressure of the woman in her lateral decubitus position for periodic intervals to obtain a stable blood pressure reading;
   b. measuring the blood pressure of the woman in her supine position as in step a, wherein the position in decubitus state and supine state is determined by a sensor and communicated to the woman by a voice/image unit;
   c. using an algorithm to compare the readings in step a and step b to determine if the woman has reached the threshold of pregnancy associated hypertension; and
   d. optionally connecting the algorithm determined outcome to a voice/image unit to convey the message to the woman or transmit the outcome to a remote clinic care unit.

11. The method according to claim 10, wherein pregnancy associated hypertension threshold is about 5-10 mmHg, about 20 mmHg, or exceeding about 20 mmHg diastolic blood pressure reading difference between the stable decubitus positon and stable supine position.

12. A method of monitoring a patient's blood pressure away from a clinical setting, comprising:
   a. measuring the blood pressure of the patient, from the lateral decubitus position for periodical intervals to obtain a stable blood pressure reading;
   b. measuring the blood pressure of the patient from the supine position as in step a, wherein the position in decubitus state and supine state is determined by an accelerometer and communicated to the woman by a voice/image unit;
   c. using an algorithm to compare the blood pressure readings of step a and step b to determine if the patient has any risk of hypertension;
   d. conveying the outcome in step c to the patient or a clinical setting via a voice/image unit; and
   e. using the voice/image unit to command the patient to stay in a position for a prolonged time period to reduce the high blood pressure or to wake up the patient in a non-acceptable body position for too long using a vibratory component.

13. A method of providing therapeutic recommendations away from a clinical setting to a patient with high blood pressure risk, comprising:
   a. measuring the blood pressure of the patient from the left lateral decubitus position for periodical intervals to obtain a stable blood pressure reading;
   b. measuring the blood pressure of the patient from the supine position as in step a, wherein the position in decubitus state and supine state is determined by a body position sensor and communicated to the woman by a voice/image unit;
   c. using an algorithm to compare the readings in step a and step b to determine if the patient has any risk of hypertension;
   d. optionally reporting the outcome of step c to the clinical setting for further analysis; and
   e. using the voice/image unit to command the patient to stay in a position for a prolonged time period to reduce the high blood pressure.

14. The method of claim 13, wherein the voice/image unit has an additional vibratory component and the method further comprises using the vibratory component to wake up the patient in a non-acceptable body position for too long.

\* \* \* \* \*